US010065984B2

(12) United States Patent
Feng et al.

(10) Patent No.: US 10,065,984 B2
(45) Date of Patent: Sep. 4, 2018

(54) POLYMORPHIC FORMS OF A STEROID-LIKE COMPOUND AND METHODS FOR THE PREPARATION AND USE THEREOF (71) Applicant: Allergan, Inc., Irvine, CA (US)

(72) Inventors: Shaoxin Feng, Tustin, CA (US); Scott W. Smith, Mission Viejo, CA (US); Olivier M. G. Lambert, Cambridge (GB); Suzanne M. Buttar, Cambridge (GB)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/568,450

(22) Filed: Dec. 12, 2014

(65) Prior Publication Data

US 2015/0166597 A1    Jun. 18, 2015

Related U.S. Application Data (60) Provisional application No. 61/915,589, filed on Dec. 13, 2013.

(51) Int. Cl.
A61K 31/573 (2006.01)
C07J 5/00 (2006.01)
C07J 7/00 (2006.01)

(52) U.S. Cl.
CPC ............. C07J 7/008 (2013.01); C07J 5/0053 (2013.01); C07B 2200/13 (2013.01)

(58) Field of Classification Search
CPC ...... C07J 7/008; C07J 5/0053; C07B 2200/13
USPC .......................................... 552/577; 514/179
See application file for complete search history.

(56) References Cited

FOREIGN PATENT DOCUMENTS

| GB | 1202626 | 8/1970 |
|---|---|---|
| JP | 52-136157 | 11/1977 |
| JP | 54-151958 | 11/1979 |
| WO | 2013-071009 | 5/2013 |
| WO | 2013-071010 | 5/2013 |

OTHER PUBLICATIONS

Database Accession No. 1978:121548, Kamano, Noriaki et al., "Steroid 17-Esters", 1978.
Database Accession No. 1982:492625, Sota, Kaoru et al., "Synthesis and Antiinflammatory Activity of Hydrocortisone 17,21-diesters", 1982.
Sota, Kaoru et al, Synthesis and Antiiflammatory Activity of Hydrocortisone 17,21-Diesters, Yakugaku Zasshi, 1982, 365-370, 102.
STN Database Accession No. 1980: 472097, Tachi, Yasuhide et al., "17.alpha.-acyloxy-21-hydroxypregnene(or diene)-3,20-diones", 1980.

Primary Examiner — Barbara P Badio
(74) Attorney, Agent, or Firm — Jonathan Bass (57) ABSTRACT Provided herein are multiple solid forms of a defined steroid-like compound, and methods for the preparation and use thereof. In one aspect, there is provided a crystalline form of said steroid-like compound, and methods for the preparation and use thereof. In another aspect, there is provided a substantially amorphous form of said steroid-like compound, and methods for the preparation and use thereof. In yet another aspect, there are provided compositions containing compounds according to the present invention. In certain aspects, such compositions are suitable for delivery of active agents according to the present invention to a subject in need thereof. In another aspect of the invention, there are provided methods for the treatment of a variety of indications, including glaucoma, ocular hypertension, and the like. In still another aspect of the present invention, there are provided kits containing compounds according to the present invention and/or compositions containing same.

7 Claims, 3 Drawing Sheets

Molecule A

Molecule B

Figure 3

POLYMORPHIC FORMS OF A STEROID-LIKE COMPOUND AND METHODS FOR THE PREPARATION AND USE THEREOF

CROSS-REFERENCE TO RELATED APPLICATIONS

The present application claims the benefit of U.S. provisional application 61/915,589 entitled "Polymorphic Forms Of A Steroid-Like Compound And Methods For The Preparation And Use Thereof" filed on Dec. 13, 2013 which is incorporated herein by reference in its entirety and serves as the basis for a priority claim for the present application.

FIELD OF THE INVENTION

The present invention relates to solid forms of a steroid-like compound, and methods for the preparation and use thereof. In one aspect, the present invention relates to crystalline forms of a steroid-like compound, and methods for the preparation and use thereof. In another aspect, the present invention relates to substantially amorphous forms of a steroid-like compound, and methods for the preparation and use thereof.

BACKGROUND OF THE INVENTION

The steroid-like compound having the structure:

is a compound with, inter alia, anti-inflammatory properties (see, e.g. British patent GB 1202626).

Many drug compounds exist in one or more crystalline forms, referred to as polymorphs. These polymorphs of the same molecule exhibit different physical properties, such as melting point, solubility, hardness, etc. In such cases, the danger exists of less soluble polymorphic forms precipitating from a solution made from another more soluble but less stable form. For example, the formation of crystals in an ophthalmic solution can cause serious injury to the eye. In addition, precipitation of the drug substance may cause an apparent reduction in potency and bioavailability of the product.

Accordingly, there is need for novel crystalline forms of compounds such as the steroid-like compound described herein.

SUMMARY OF THE INVENTION

In accordance with the present invention, there are provided multiple solid forms of a steroid-like compound, and methods for the preparation and use thereof.

In one aspect of the present invention, there are provided crystalline forms of a steroid-like compound, and methods for the preparation and use thereof. In another aspect, there are provided substantially amorphous forms of a steroid-like compound, and methods for the preparation and use thereof.

In accordance with yet another aspect of the present invention, there are provided compositions containing said steroid-like compound. In certain aspects, such compositions are suitable for delivery of said steroid-like compound to a subject in need thereof. In certain aspects, there are provided methods for the treatment of a variety of indications, including glaucoma, dry eye disease, ocular hypertension, and the like.

In accordance with a further aspect of the present invention, there are provided kits containing said steroid-like compound and/or compositions containing same.

DETAILED DESCRIPTION OF THE INVENTION

In accordance with the present invention, there are provided solid forms of the steroid-like compound having the structure:

In certain embodiments of the invention, the solid form of said steroid-like compound is crystalline (Form 1). Such crystalline form can be further characterized by the X-ray powder diffraction (XRPD) pattern thereof. An exemplary XRPD pattern for crystalline Form 1 has peaks at least at about 7.4, 10.2, 11.4, 12.4, 14.3, 14.7, 17.4, 20.2, 22.4 and 31.6 degrees 2θ.

Figure 1:
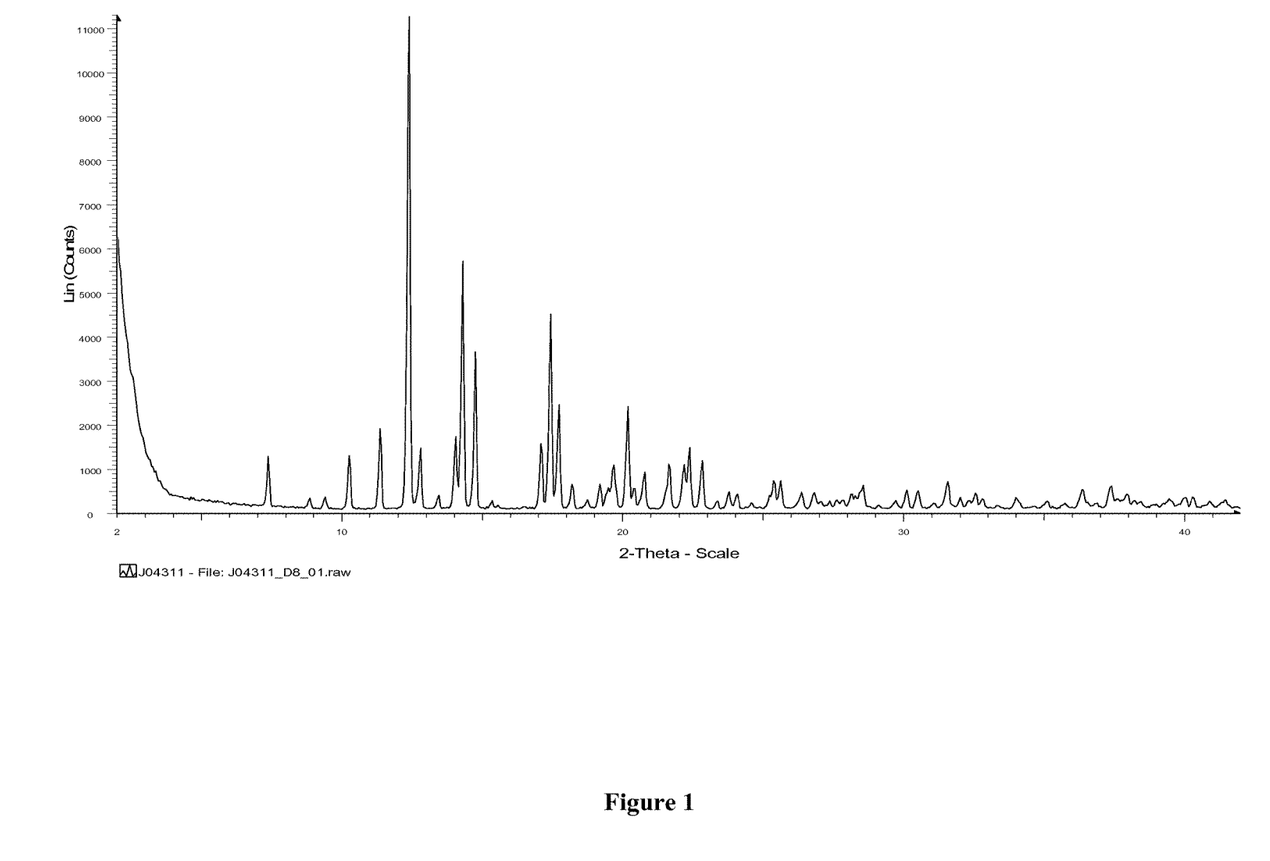
FIG. 1 presents an exemplary X-ray powder diffraction (XRPD) pattern for crystalline Form 1 of the steroid-like compound described herein. Major peaks unique to Form 1 include peaks at least at about 7.4, 10.2, 11.4, 12.4, 14.3, 14.7, 17.4, 20.2, 22.4 and 31.6 degrees 2θ. The vertical scale is from 0 to 11300, and the horizontal scale is from 2 to 42.

An exemplary XRPD pattern for crystalline Form 1 is substantially as shown in FIG. 1. A skilled person would realize that, in general, the position of the 2θ peaks in an XRPD pattern can vary by approximately 0.1, and thus exemplary peaks of the crystal form herein described would appear at about (2θ) 7.4, 10.2, 11.4, 12.4, 14.3, 14.7, 17.4, 20.2, 22.4 and 31.6, wherein the term "about" indicates peaks at (2θ) 7.4±0.1, 10.2±0.1, 11.4±0.1, 12.4±0.1, 14.3±0.1, 14.7±0.1, 17.4±0.1, 20.2±0.1, 22.4±0.1 and 31.6±0.1 in an XRPD pattern. A skilled person would also understand that similar variations would apply to the other 2θ peaks in FIG. 1 which can also vary by approximately 0.1.

In some embodiments of the present invention, crystalline Form 1 has a melting endotherm commencing at about 219° C. (with a peak at about 221° C.) and a decomposition endotherm commencing at about 225° C.

Crystalline Form 1 can be further characterized as remaining substantially unchanged even if exposed to elevated temperatures and/or humidity. Indeed, such conditions tend to promote the formation of crystalline Form 1 from the amorphous form of the steroid-like compound described herein.

Crystalline Form 1 can still further be characterized as remaining substantially unchanged even if stored at or about room temperature for extended periods of time (e.g., at least 6 months, at least 1 year, at least 2 years).

As used herein, "substantially unchanged" means that the indicia that a sample exists in crystalline Form 1 (e.g., the presence of the unique XRPD peaks referred to herein) remain clearly discernible.

Figure 2:
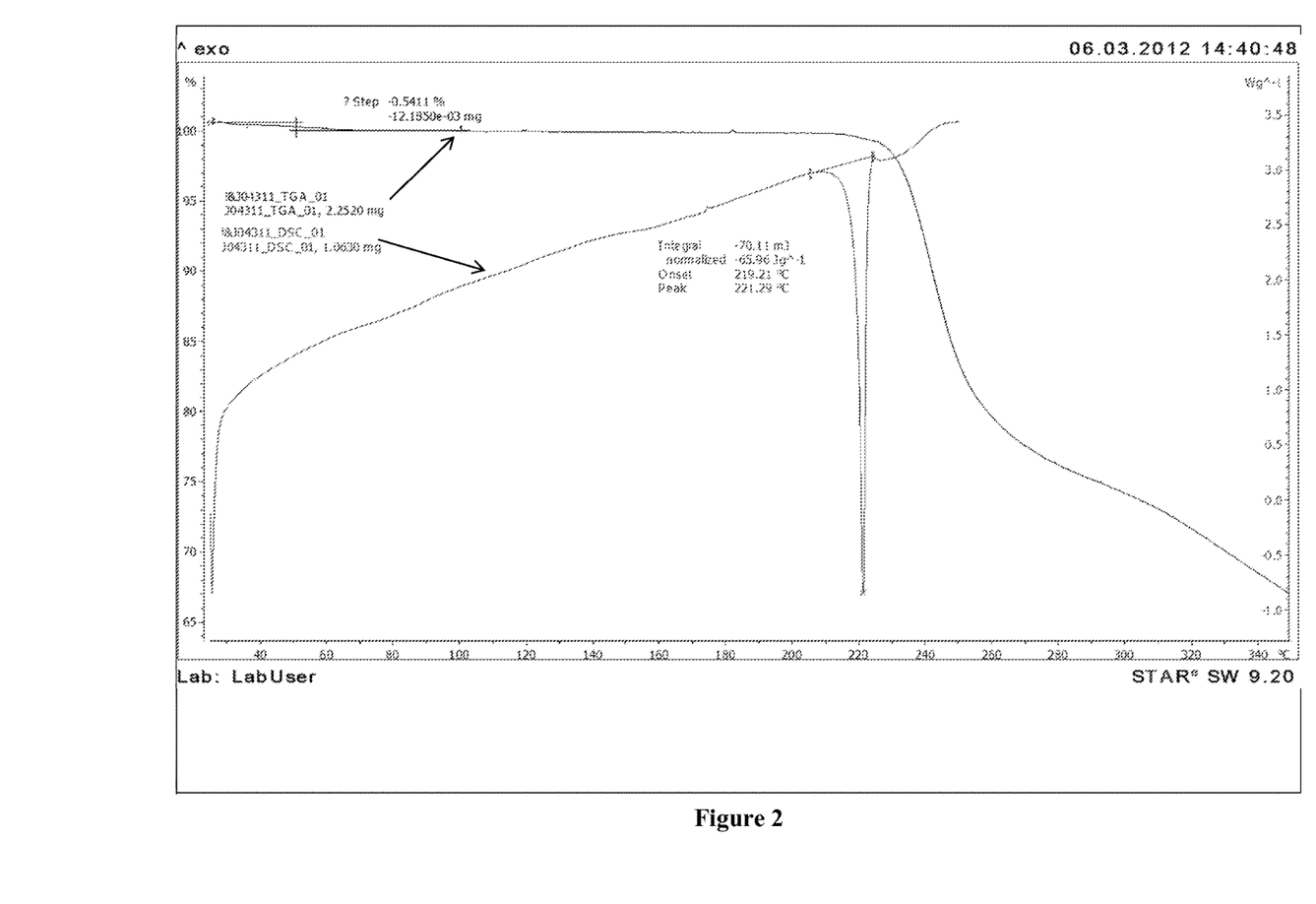
FIG. 2 presents thermogravimetric analysis/differential scanning calorimetry (TGA/DSC) curves for crystalline solid Form 1 of the steroid-like compound described herein. Melting of Form 1 starts at about 219° C., with a peak at about 221° C. Decomposition of the compound appears to begin shortly thereafter (at about 225° C.).

Crystalline Form 1 can also be characterized with reference to the differential scanning calorimetry (DSC) profile thereof; an exemplary DSC profile thereof is as shown in FIG. 2.

Crystalline Form 1 can alternatively be characterized with reference to the structural features of a single crystal thereof, i.e., crystals having orthorhombic space group $P2_12_12_1$ with unit cell dimensions:

a=10.1122(5) Å,
b=10.2108(4) Å,
c=47.7048(13) Å,
α=β=γ=90°,
V=4925.7(3) Å$^3$, Z=8, Density=1.258 g/cm and T=100(2) K.

In some embodiments, crystalline Form 1 can be characterized with reference to the X-ray atomic coordinates of each element thereof. See, for example, Table 1.

TABLE 1

| Elements | x | y | z | U (eq) (Å$^2$) |
|---|---|---|---|---|
| C1A | 0.3927(6) | 0.4038(4) | 0.90360(8) | 0.0305(10) |
| C2A | 0.5098(6) | 0.4810(4) | 0.91511(8) | 0.0350(11) |
| C3A | 0.6469(6) | 0.4187(4) | 0.91282(9) | 0.0359(11) |
| C4A | 0.3854(5) | 0.4046(4) | 0.87080(8) | 0.0299(10) |
| C5A | 0.3987(6) | 0.5490(4) | 0.86166(9) | 0.0365(11) |
| C6A | 0.4804(5) | 0.3152(4) | 0.85491(8) | 0.0308(10) |
| C7A | 0.4476(5) | 0.3047(5) | 0.82350(8) | 0.0314(10) |
| C8A | 0.3008(5) | 0.2669(4) | 0.81863(8) | 0.0292(10) |
| C9A | 0.2612(5) | 0.2573(4) | 0.78686(8) | 0.0321(10) |
| C10A | 0.2487(6) | 0.3909(5) | 0.77191(9) | 0.0386(12) |
| C11A | 0.3625(5) | 0.1700(5) | 0.77191(8) | 0.0354(11) |
| C12A | 0.3155(6) | 0.1224(5) | 0.74322(9) | 0.0402(13) |
| C13A | 0.1834(6) | 0.0582(5) | 0.74481(9) | 0.0369(12) |
| C14A | 0.0947(6) | 0.0978(5) | 0.76737(9) | 0.0396(12) |
| C15A | 0.1254(5) | 0.1931(5) | 0.78564(9) | 0.0343(11) |
| C16A | 0.0217(6) | 0.2511(5) | 0.80431(9) | 0.0390(11) |
| C17A | 0.0657(6) | 0.2731(4) | 0.83448(9) | 0.0347(11) |
| C18A | 0.1993(5) | 0.3448(4) | 0.83610(8) | 0.0316(10) |
| C19A | 0.2423(5) | 0.3523(4) | 0.86668(8) | 0.0294(10) |
| C20A | 0.1611(6) | 0.4342(4) | 0.88738(9) | 0.0359(11) |
| C21A | 0.2545(5) | 0.4549(4) | 0.91258(9) | 0.0374(12) |
| C22A | 0.4171(5) | 0.2420(4) | 0.93904(8) | 0.0299(10) |
| C23A | 0.4177(5) | 0.0991(4) | 0.94539(9) | 0.0311(10) |
| C24A | 0.4404(6) | 0.0626(5) | 0.97293(10) | 0.0394(12) |
| C25A | 0.4396(7) | −0.0689(5) | 0.98016(10) | 0.0471(14) |

TABLE 1-continued

| Elements | x | y | z | U (eq) (Å$^2$) |
|---|---|---|---|---|
| C26A | 0.4173(6) | −0.1625(4) | 0.95984(11) | 0.0440(13) |
| C27A | 0.3949(6) | −0.1264(5) | 0.93241(10) | 0.0429(13) |
| C28A | 0.3951(6) | 0.0044(4) | 0.92496(9) | 0.0355(11) |
| H2AA | 0.7464 | 0.4621 | 0.9442 | 0.058 |
| H3AA | 0.6424 | 0.328 | 0.9201 | 0.043 |
| H3AB | 0.672 | 0.4138 | 0.8928 | 0.043 |
| H3AC | 0.5436 | 0.4582 | 0.8162 | 0.061 |
| H5AA | 0.3656 | 0.559 | 0.8425 | 0.055 |
| H5AB | 0.492 | 0.575 | 0.8624 | 0.055 |
| H5AC | 0.3472 | 0.6047 | 0.8743 | 0.055 |
| H6AA | 0.4776 | 0.2267 | 0.8633 | 0.037 |
| H6AB | 0.5716 | 0.3492 | 0.857 | 0.037 |
| H7AA | 0.5034 | 0.2329 | 0.8155 | 0.038 |
| H8AA | 0.2937 | 0.1751 | 0.8258 | 0.035 |
| H10A | 0.2155 | 0.3774 | 0.7528 | 0.058 |
| H10B | 0.3356 | 0.4332 | 0.7711 | 0.058 |
| H10C | 0.187 | 0.4467 | 0.7823 | 0.058 |
| H11A | 0.4458 | 0.2197 | 0.7695 | 0.043 |
| H11B | 0.3818 | 0.0931 | 0.7839 | 0.043 |
| H12A | 0.3106 | 0.1978 | 0.7302 | 0.048 |
| H12B | 0.3806 | 0.0594 | 0.7356 | 0.048 |
| H14A | 0.012 | 0.0545 | 0.7692 | 0.047 |
| H16A | −0.0563 | 0.1924 | 0.8044 | 0.047 |
| H16B | −0.0066 | 0.3361 | 0.7963 | 0.047 |
| H17A | 0.0733 | 0.1874 | 0.8441 | 0.042 |
| H17B | −0.0023 | 0.3252 | 0.8444 | 0.042 |
| H18A | 0.1899 | 0.4352 | 0.8283 | 0.038 |
| H19A | 0.2417 | 0.2605 | 0.874 | 0.035 |
| H20A | 0.0801 | 0.3869 | 0.8931 | 0.043 |
| H20B | 0.1355 | 0.5191 | 0.879 | 0.043 |
| H21A | 0.222 | 0.4057 | 0.9291 | 0.045 |
| H21B | 0.2592 | 0.5489 | 0.9175 | 0.045 |
| H24A | 0.4563 | 0.1274 | 0.9868 | 0.047 |
| H25A | 0.4545 | −0.0944 | 0.999 | 0.056 |
| H26A | 0.4174 | −0.2526 | 0.9648 | 0.053 |
| H27A | 0.3793 | −0.1916 | 0.9186 | 0.051 |
| H28A | 0.38 | 0.0295 | 0.9061 | 0.043 |
| O1A | 0.4978(4) | 0.5901(3) | 0.92428(6) | 0.0381(8) |
| O2A | 0.7455(4) | 0.4867(3) | 0.92739(6) | 0.0386(8) |
| O3A | 0.4785(4) | 0.4213(4) | 0.80862(6) | 0.0409(9) |
| O4A | 0.1454(4) | −0.0203(4) | 0.72694(6) | 0.0470(10) |
| O5A | 0.4062(4) | 0.2655(3) | 0.91140(5) | 0.0299(7) |
| O6A | 0.4261(4) | 0.3279(3) | 0.95646(6) | 0.0389(8) |
| C1B | −0.1701(5) | −0.1821(5) | 0.84613(9) | 0.0308(10) |
| C2B | −0.2410(5) | −0.3045(5) | 0.83526(8) | 0.0346(11) |
| C3B | −0.1713(6) | −0.4353(5) | 0.83828(9) | 0.0367(11) |
| C4B | −0.1757(5) | −0.1676(5) | 0.87881(9) | 0.0315(10) |
| C5B | −0.3207(5) | −0.1870(5) | 0.88767(9) | 0.0370(11) |
| C6B | −0.0830(5) | −0.2524(4) | 0.89594(8) | 0.0283(9) |
| C7B | −0.0780(6) | −0.2121(4) | 0.92717(8) | 0.0322(10) |
| C8B | −0.0474(5) | −0.0643(4) | 0.93082(8) | 0.0287(10) |
| C9B | −0.0437(5) | −0.0192(4) | 0.96223(8) | 0.0307(10) |
| C10B | −0.1800(6) | −0.0137(5) | 0.97660(10) | 0.0408(13) |
| C11B | 0.0514(6) | −0.1093(4) | 0.97818(8) | 0.0346(11) |
| C12B | 0.0931(6) | −0.0529(5) | 1.00660(9) | 0.0395(12) |
| C13B | 0.1502(6) | 0.0813(5) | 1.00393(9) | 0.0393(12) |
| C14B | 0.1045(6) | 0.1608(5) | 0.98076(9) | 0.0358(11) |
| C15B | 0.0129(6) | 0.1214(4) | 0.96235(9) | 0.0326(11) |
| C16B | −0.0537(6) | 0.2158(4) | 0.94286(9) | 0.0357(11) |
| C17B | −0.0689(6) | 0.1637(4) | 0.91281(9) | 0.0346(11) |
| C18B | −0.1317(5) | 0.0267(4) | 0.91212(9) | 0.0307(10) |
| C19B | −0.1308(5) | −0.0249(4) | 0.88190(8) | 0.0295(10) |
| C20B | −0.2149(5) | 0.0480(4) | 0.86025(9) | 0.0337(10) |
| C21B | −0.2271(6) | −0.0500(5) | 0.83569(9) | 0.0371(11) |
| C22B | −0.0016(5) | −0.2054(4) | 0.81147(8) | 0.0301(10) |
| C23B | 0.1417(5) | −0.2001(5) | 0.80573(9) | 0.0331(10) |
| C24B | 0.1836(6) | −0.2288(6) | 0.77854(10) | 0.0441(13) |
| C25B | 0.3164(7) | −0.2237(6) | 0.77198(11) | 0.0506(15) |
| C26B | 0.4072(7) | −0.1907(6) | 0.79199(12) | 0.0507(14) |
| C27B | 0.3688(6) | −0.1628(5) | 0.81919(11) | 0.0429(12) |
| C28B | 0.2343(5) | −0.1661(5) | 0.82600(9) | 0.0353(11) |
| H2BA | −0.2191 | −0.5468 | 0.8089 | 0.06 |
| H3BA | −0.0827 | −0.4294 | 0.8295 | 0.044 |
| H3BB | −0.1588 | −0.4547 | 0.8584 | 0.044 |
| H3BC | −0.2176 | −0.3223 | 0.9374 | 0.06 |
| H5BA | −0.3337 | −0.1515 | 0.9066 | 0.055 |
| H5BB | −0.3419 | −0.2806 | 0.8876 | 0.055 |
| H5BC | −0.3788 | −0.1411 | 0.8745 | 0.055 |

TABLE 1-continued

| Elements | x | y | z | U (eq) (Å²) |
|---|---|---|---|---|
| H6BA | 0.0071 | −0.2466 | 0.8879 | 0.034 |
| H6BB | −0.1121 | −0.3448 | 0.8946 | 0.034 |
| H7BA | −0.0035 | −0.2615 | 0.936 | 0.039 |
| H8BA | 0.0453 | −0.0534 | 0.9239 | 0.034 |
| H10D | −0.1707 | 0.0247 | 0.9953 | 0.061 |
| H10E | −0.2159 | −0.1026 | 0.9782 | 0.061 |
| H10F | −0.2403 | 0.0401 | 0.9654 | 0.061 |
| H11C | 0.0081 | −0.1952 | 0.9812 | 0.042 |
| H11D | 0.1312 | −0.1242 | 0.9666 | 0.042 |
| H12C | 0.0152 | −0.0497 | 1.0192 | 0.047 |
| H12D | 0.1595 | −0.1116 | 1.0153 | 0.047 |
| H14B | 0.1415 | 0.2457 | 0.9785 | 0.043 |
| H16C | −0.0018 | 0.298 | 0.9423 | 0.043 |
| H16D | −0.1424 | 0.2371 | 0.9504 | 0.043 |
| H17C | −0.1247 | 0.2249 | 0.9019 | 0.041 |
| H17D | 0.0192 | 0.1601 | 0.9038 | 0.041 |
| H18B | −0.2244 | 0.0307 | 0.9193 | 0.037 |
| H19B | −0.0371 | −0.0208 | 0.8752 | 0.035 |
| H20C | −0.1708 | 0.1297 | 0.8541 | 0.04 |
| H20D | −0.303 | 0.0699 | 0.868 | 0.04 |
| H21C | −0.1766 | −0.0183 | 0.8193 | 0.044 |
| H21D | −0.3208 | −0.0604 | 0.8302 | 0.044 |
| H24B | 0.1207 | −0.2517 | 0.7646 | 0.053 |
| H25B | 0.3449 | −0.2431 | 0.7535 | 0.061 |
| H26B | 0.4982 | −0.187 | 0.7872 | 0.061 |
| H27B | 0.4329 | −0.1416 | 0.833 | 0.051 |
| H28B | 0.2063 | −0.1451 | 0.8445 | 0.042 |
| O1B | −0.3533(4) | −0.2981(4) | 0.82634(6) | 0.0398(8) |
| O2B | −0.2425(4) | −0.5389(3) | 0.82571(6) | 0.0401(8) |
| O3B | −0.1943(4) | −0.2462(3) | 0.94192(6) | 0.0399(9) |
| O4B | 0.2258(4) | 0.1270(4) | 1.02163(6) | 0.0451(10) |
| O5B | −0.0289(3) | −0.1901(3) | 0.83923(6) | 0.0312(7) |
| O6B | −0.0865(4) | −0.2215(4) | 0.79397(6) | 0.0393(8) |

Figure 3:
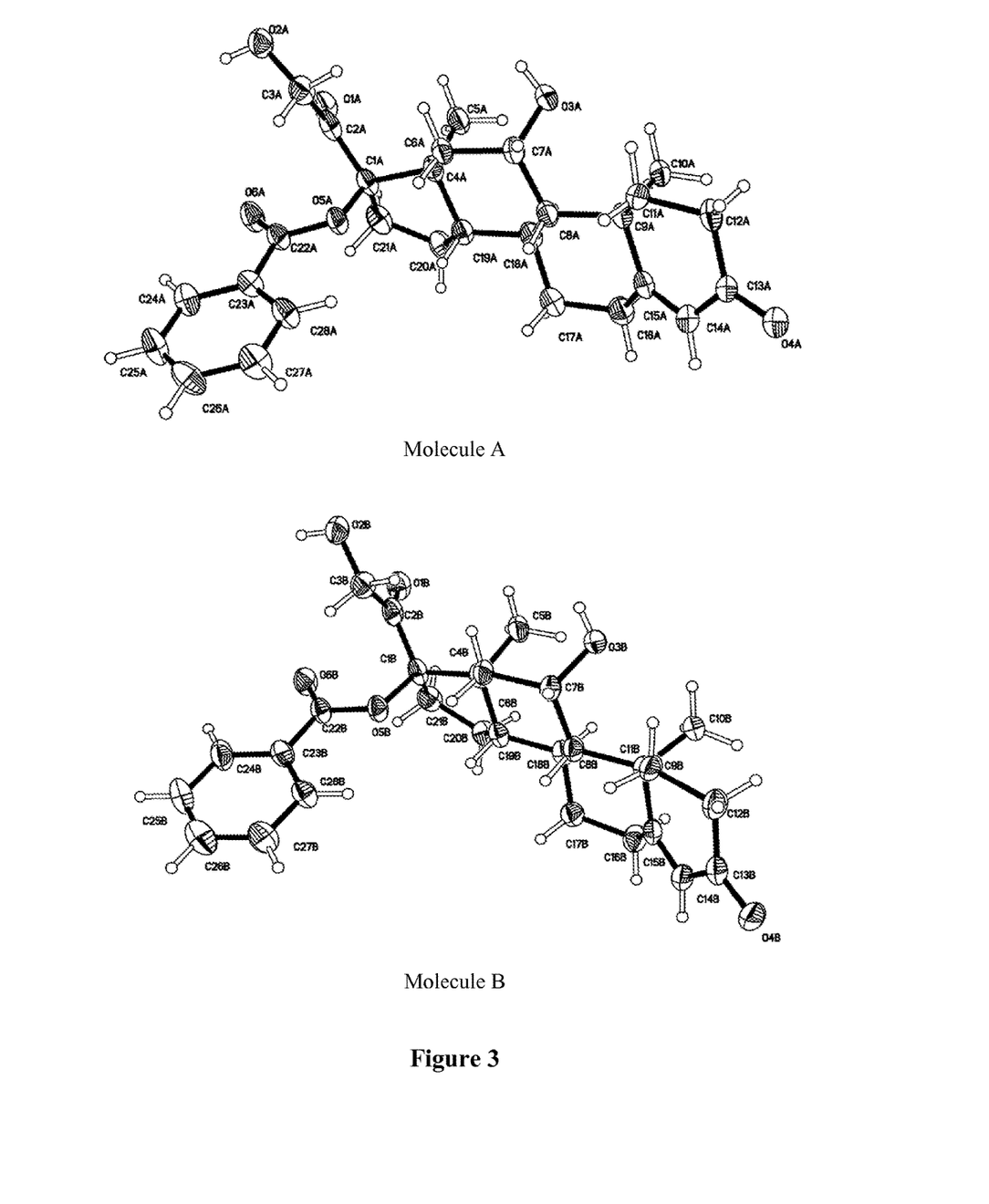
FIG. 3 presents a molecular model of molecular configurations A and B of crystalline Form 1 of the steroid-like compound described herein.

In some embodiments, there are two molecules in the asymmetric unit of the crystal lattice of Form 1. FIG. 3 shows the molecular configurations of the two molecules (molecule A and B).

In some embodiments of the present invention, crystalline Form 1 is substantially free of other solid forms. As used herein, "substantially free" refers to samples wherein the presence of alternate solid forms falls below the detection limit, i.e., less than about 10% of said solid is in a form other than crystalline Form 1.

In addition, the crystalline form described herein has a differential scanning calorimetry profile as shown in FIG. 2, including having a melting endotherm commencing at about 219° C. (with a peak at about 221° C.) and a decomposition endotherm commencing at about 225° C. in its differential scanning calorimetry profile. This profile shows a single melting event indicating that Form 1 is essentially a pure crystal and does not contain any other crystalline forms. Accordingly, a skilled person would understand that the crystalline form described herein can be substantially free of other crystalline forms based on its DSC profile.

In certain embodiments of the invention, the solid form of the steroid-like compound contemplated for use herein is substantially amorphous. As used herein, "substantially amorphous" refers to samples wherein the majority of the active compound therein has no indicia of crystal structure, e.g., wherein XRPD analysis reveals no discernible peaks in an XRPD evaluation thereof.

In accordance with another embodiment of the present invention, there are provided pharmaceutical compositions comprising a therapeutically effective amount of:
  crystalline Form 1 as described herein,
  a substantially amorphous form of said steroid-like compound, or
  combinations of any two or more thereof,
in an ophthalmically acceptable carrier therefore.

Those skilled in the art can readily identify ophthalmically acceptable carriers suitable for administration (or the manufacture of medicaments containing) the steroid-like compounds disclosed herein. Specifically, a drug to be administered systemically may be confected as a solution, emulsion, suspension, aerosol, or the like.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions according to the present invention include, but are not limited to, benzalkonium chloride, chlorobutanol, thimerosal, phenylmercuric acetate, phenylmercuric nitrate, and the like. A useful surfactant is, for example, Tween 80. Likewise, various useful vehicles may be used in the ophthalmic preparations according to the present invention. These vehicles include, but are not limited to, polyvinyl alcohol, povidone, hydroxypropyl methyl cellulose, poloxamers, carboxymethyl cellulose, hydroxyethyl cellulose, purified water, and the like.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers including acetate buffers, citrate buffers, phosphate buffers, borate buffers, and the like, are contemplated for use herein. Acids or bases may be used to adjust the pH of these formulations as needed.

In a similar vein, an ophthalmically acceptable antioxidant for use in accordance with the present invention includes, but is not limited to, sodium metabisulfite, sodium thiosulfate, acetylcysteine, butylated hydroxyanisole, butylated hydroxytoluene, and the like.

Other excipient components which may be included in the ophthalmic preparations contemplated herein are chelating agents. A useful chelating agent is edetate disodium, although other chelating agents may also be used in place of, or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |

| Ingredient | Amount (% w/v) |
| --- | --- |
| antioxidant | as needed |
| surfactant | as needed |
| purified water | as needed to make 100% |

The amount of the steroid-like compound administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. Therapeutically effective dosages contemplated for steroid-like compounds according to the present invention may be in the range of about 0.5 or about 1 to about 100 mg/kg/day.

In one embodiment of the present invention, compositions described herein are packaged in a dropper for ophthalmic application.

Compounds according to the present invention are useful for the treatment of a variety of indications, e.g., inflammatory eye conditions (e.g., dry eye disease, conjunctivitis, and the like), glaucoma, and the like.

In accordance with one aspect of the present invention, use of compounds according to the invention in the treatment and/or prevention, and/or in the manufacture of a medicament for the treatment and/or prevention, of any of the above-referenced diseases and/or conditions is also contemplated.

Therefore, in accordance with yet another embodiment of the present invention, there are provided methods for reducing ocular hypertension comprising administering to a subject in need thereof a therapeutically effective amount of a composition as described herein.

In accordance with still another embodiment of the present invention, there are provided methods for treating glaucoma comprising administering to a subject in need thereof a therapeutically effective amount of a composition as described herein.

In one embodiment of the above-referenced methods, the compositions according to the present invention are administered via topical administration to an eye.

In another embodiment, the present invention provides for a method for treating dry eye disease comprising administering to a subject in need thereof a composition comprising the steroid-like compound in crystalline Form 1 as described herein.

In another embodiment, the present invention provides for a method for treating dry eye disease comprising administering to a subject in need thereof a composition comprising the steroid-like compound in a substantially amorphous as described herein.

"Treatment," "treat," or any other form of these words as used herein are intended to mean use in the diagnosis, cure, mitigation, treatment, or prevention of disease in man or other animals.

In accordance with yet another embodiment of the present invention, there are provided methods for preparing defined solid forms of the steroid-like compound described herein employing one or more of the following crystallization techniques, e.g., evaporation, cooling, slurry, vapor diffusion, and the like.

In accordance with a further embodiment of the present invention, there are provided methods for preparing crystalline Form 1 of the steroid-like compound described herein from the amorphous state thereof, said method comprising subjecting an optionally warmed suspension and/or a solution of said compound to:
(i) conditions suitable for evaporation of diluent therefrom,
(ii) thermocycling/maturation (between room temperature and 50° C.) in nonpolar solvent in the presence of crystalline or amorphous forms of the steroid-like compound, and
(iii) gradually:
reducing the temperature thereof, and/or
adding sufficient non-solvent thereto to promote precipitation of said compound therefrom.

As used herein, "suitable diluent" refers to media in which the steroid-like compound can be suspended and/or dissolved. Exemplary diluents include ketones (e.g., acetone, methyl ethyl ketone, and the like), alcohols (e.g., methanol, ethanol, propanol, butanol, and the like), esters (e.g., ethyl acetate), nitriles (e.g., acetonitrile), ethers (e.g., diethyl ether, methyl tert-butyl ether, tetrahydrofuran, 2-methyltetrahydrofuran, dioxane, and the like), alkanes (e.g., hexane, heptane, and the like), chlorinated hydrocarbons (e.g., dichloromethane, chloroform, and the like), aromatics (e.g., benzene, toluene, and the like), as well as mixtures of any two or more thereof.

As used herein, "conditions suitable for evaporation of diluent therefrom" refers to the combination of temperature and/or atmospheric pressure that promotes removal of diluent from a suspension or solution. For example, elevated temperatures at atmospheric pressure can be employed; alternatively, ambient temperature can be employed at reduced pressures; or the combination of elevated temperature and reduced pressure can be employed to promote evaporation of diluent from a suspension or solution containing a steroid-like compound according to the present invention.

As used herein, "suitable non-polar solvent" refers to a solvent of sufficiently low polarity to induce crystal formation of said steroid-like compound.

As used herein, "time sufficient for crystals . . . to form" refers to the amount of time required for a given sample to equilibrate into the solid form preferred under the particular conditions. The amount of time required to do so can vary from minutes to days; typically 1-14 days is adequate for such purpose.

As used herein, "non-solvent" refers to medium in which the steroid-like compound described herein is not appreciably soluble; therefore, the use of "sufficient" non-solvent contemplates the addition of a quantity of non-solvent sufficient to induce precipitation and/or crystallization of the majority of said compound from a solution or suspension containing same.

In accordance with a further embodiment of the present invention, there are provided methods for converting the amorphous form of the steroid-like compounds described herein into crystalline Form 1 thereof, said method comprising subjecting said compound to elevated humidity (e.g., a relative humidity >50%) and/or temperature (e.g., a temperature of at least 35° C.) for at least 72 hours.

In certain embodiments, a substantially amorphous form of the steroid-like compound contemplated for use herein can be converted into crystalline Form 1 by subjecting said amorphous material to elevated temperatures and/or elevated humidity sufficient to promote the desired conversion. For example, it has been determined that exposure of substantially amorphous material to a temperature higher than about 110° C. for at least about 1 hour is sufficient to promote conversion of a substantial portion thereof to crystalline Form 1. Similarly, exposure of substantially amorphous material to 97% relative humidity at room temperature (about 25° C.) for about 2 weeks is sufficient to promote conversion of a substantial portion thereof to crystalline Form 1. Alternatively, exposure of substantially amorphous material to 75% relative humidity at about 40° C. for about 1 week has also been found to be sufficient to promote conversion of a substantial portion thereof to crystalline Form 1.

As used herein, "substantial portion thereof" refers to the major portion of the sample in question, i.e., greater than 50% of the sample, undergoes conversion from the amorphous form thereof to crystalline Form 1; in some embodiments, greater than 60% of the sample undergoes conversion from the amorphous form thereof to crystalline Form 1; in some embodiments, greater than 70% of the sample undergoes conversion from the amorphous form thereof to crystalline Form 1; in some embodiments, greater than 80% of the sample undergoes conversion from the amorphous form thereof to crystalline Form 1; in some embodiments, greater than 90% of the sample undergoes conversion from the amorphous form thereof to crystalline Form 1.

In accordance with a further embodiment of the present invention, there are provided methods for converting Form 1 of the steroid-like compound described herein into the amorphous form thereof, said method comprising freeze-drying material of Form 1 using a suitable diluent such as a t-butanol/water mixture (v/v 3/1) and a suitable freeze-drying cycle such as freezing at dry ice/acetone temperatures for about 10 minutes followed by a 12 hour drying cycle.

In accordance with another aspect of the present invention, there are provided kits comprising the compositions described herein, a container, and instructions for administration of said composition to a subject in need thereof for the mitigation of glaucoma, ocular hypertension, or the like.

The actual dose of the active compounds of the present invention depends on the specific compound, and on the condition to be treated; the selection of the appropriate dose is well within the knowledge of the skilled artisan.

For treatment of diseases affecting the eye including glaucoma, these compounds can be administered topically, periocularly, intraocularly, or by any other effective means known in the art.

For the treatment of glaucoma, combination treatment with the following classes of drugs is contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as charbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, latanoprost and the like.

EXAMPLES

Various aspects of the present invention are illustrated by the following non-limiting examples. The examples are for illustrative purposes and are not a limitation on any practice of the present invention. It will be understood that variations and modifications can be made without departing from the spirit and scope of the invention. One of ordinary skill in the art readily knows how to synthesize or commercially obtain the reagents and components described herein.

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. Samples were run under ambient conditions as flat plate specimens. The sample was gently packed into a cavity cut into polished, zero-background (510) silicon wafer. The parameters of the data collection are:

Angular range: 2 to 42°2θ

Step size: 0.05°2θ

Collection time: 0.5 s/step

DSC data were collected on a Mettler DSC 823E. Typically 1-3 mg of each sample, in a pin-holed aluminum pan, was heated at 10° C./min from 25° C. to 260° C. A nitrogen purge at 50 ml/min was maintained over the sample.

The steroid-like compound described herein can be synthesized according to procedures given in British patent GB 1202626. For the examples below, the amorphous form of the steroid-like compound was prepared by freeze-drying a supplied crystalline form according to the following procedure: the steroid-like compound as supplied (crystalline) was dissolved in 40 volume equivalents of a t-butanol/water mixture (75/25% vol.) at 50° C. The resulting solution was then filtered (0.45 μm filter) in order to ensure no crystalline seeds were present and treated as follows: (1.4 g batch) freezing in dry ice/acetone for 10 minutes followed by a 12 hour drying under vacuum. Temperature was not controlled during the drying stage.

Example 1

A warm solution of the steroid-like compound described herein was prepared in a variety of solvents, such as acetonitrile, acetone, dimethylformamide, methanol, ethanol, ethyl acetate, 1-propanol, 2-propanol, or a mixture of acetone and water (v/v 9/1), or acetonitrile and water (v/v 9/1) then allowed to slowly cool until crystals were observed. The combination of solvents/cooling conditions which facilitated formation of crystalline Form 1 is summarized in Table 2:

TABLE 2

| Solvent | Conditions |
| --- | --- |
| Acetonitrile | 50° C. → 4° C. |
| Acetone | 50° C. → −20° C. |
| Ethyl acetate | 50° C. → 4° C. |
| Methanol | 50° C. → room temperature |
| 2-propanol | 50° C. → 4° C. |
| Acetone/water (v/v 9/1) | 50° C. → 4° C. |
| Acetonitrile/water (v/v 9/1) | 50° C. → −20° C. |

Example 2

The steroid-like compound described herein was dissolved in a suitable solvent such as anisole, dichloromethane, dioxane, tetrahydrofuran, chloroform, heptane, or a mixture of dioxane and water (v/v 9/1). Evaporation of the solvent therefrom provided crystalline Form 1, as determined by XRPD.

Example 3

It is expected that the steroid-like compound described herein can also be crystallized employing vapor diffusion techniques. In particular, it is expected that crystalline Form 1 can be obtained when said compound is dissolved in a polar solvent such as acetonitrile, and then exposed to a non-polar solvent such as toluene at room temperature.

Alternatively, it is expected that crystalline Form 1 can be obtained when said compound is dissolved in a polar solvent such as dioxane, and then exposed to a non-aromatic, non-polar solvent such as hexane at room temperature.

Example 4

Alternatively, it is expected that crystalline Form 1 can be obtained by thermocycling/maturation (between room temperature and 50° C.) in nonpolar solvent such as toluene in the presence of crystalline or amorphous forms of the steroid-like compound contemplated for use herein.

Example 5

A sample of the steroid-like compound in crystalline Form 1 was stored for 7 days at 40° C. and 75% relative humidity. After that time an XRPD spectrum was obtained and compared to the XRPD spectrum of the sample before the storage at the elevated temperature and humidity. No noticeable change in the XRPD spectrum was found. Similarly, another sample of the steroid-like compound in crystalline Form 1 was stored for 1 year at room temperature (21° C. and uncontrolled relative humidity). Comparison of the XRPD spectrum after the storage at room temperature to the XRPD spectrum before the storage at room temperature also revealed no change. These results indicate that the steroid-like compound in crystalline Form 1 remains in crystal Form 1 even after storage for prolonged periods of time at elevated temperature and humidity and at room temperature.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

That which is claimed is:

1. A method for preparing crystalline form 1, having an X-ray powder diffraction pattern with peaks at about 7.4, 10.2, 11.4, 12.4, 14.3, 14.7, 17.4, 20.2, 22.4 and 31.6 degrees 2θ, of the compound:

said method comprising:
dissolving the compound in a suitable diluent selected from the group consisting of anisole, dichloromethane, dioxane, tetrahydrofuran, chloroform, heptane, and a 9:1 (v:v) mixture of dioxane and water, and
subjecting the solution of the compound in the diluent to conditions suitable for evaporation of the diluent therefrom, wherein the conditions suitable for the evaporation of the diluent therefrom are selected from the group consisting of elevated temperatures at atmospheric pressure, ambient temperature at reduced pressures, and a combination of elevated temperature and reduced pressure.

2. The method of claim 1, wherein the conditions suitable for evaporation of diluent comprise elevated temperatures at atmospheric pressure.

3. The method of claim 1, wherein the conditions suitable for evaporation of diluent comprise ambient temperature at reduced pressures.

4. The method of claim 1, wherein the conditions suitable for evaporation of diluent comprise a combination of elevated temperature and reduced pressure.

5. A method for converting amorphous form of the compound:

into crystalline form 1, having an X-ray powder diffraction pattern with peaks at about 7.4, 10.2, 11.4, 12.4, 14.3, 14.7, 17.4, 20.2, 22.4 and 31.6 degrees 2θ, said method comprising subjecting said compound to elevated humidity and/or temperature for at least 72 hours.

6. The method of claim 5, wherein the elevated humidity is a relative humidity of greater than 50%.

7. The method of claim 5, wherein the elevated temperature is a temperature of at least 35° C.

* * * * *